United States Patent [19]
Yarosh

[11] Patent Number: 5,352,458
[45] Date of Patent: Oct. 4, 1994

[54] TANNING METHOD USING DNA REPAIR LIPOSOMES

[75] Inventor: Daniel B. Yarosh, Merrick, N.Y.

[73] Assignee: Applied Genetics Inc., Freeport, N.Y.

[21] Appl. No.: 995,262

[22] Filed: Dec. 21, 1992

[51] Int. Cl.$^5$ ............................................. A61K 9/127
[52] U.S. Cl. ................................... 424/450; 424/59;
424/401; 435/174; 435/175; 435/177; 435/182
[58] Field of Search .................. 424/450, 59, 401, 420;
436/829; 428/402.2; 435/174, 175, 177, 182

[56] References Cited

U.S. PATENT DOCUMENTS 5,077,211  12/1991  Yarosh ................................ 435/193

FOREIGN PATENT DOCUMENTS

WO90/00598  1/1990  PCT Int'l Appl. .

OTHER PUBLICATIONS

Kibitel et al. Photochem. & Photobid. 54 #5, 753, 1991.
Yarosh et al. J. Soc. Cosmet. Chem 41, 85, 1990.
Yarosh et al. Can. Res. 52, 4227, 1992.
Ceccoli et al., "Encapsulation of the UV-DNA Repair Enzyme T4 Endonuclease V in Liposomes and Delivery to Human Cells", *J. Invest. Dermatol.*, vol. 93, pp. 190-194, Aug. 1989.
Kibitel et al., "Enhancement of Ultraviolet-DNA Repair in denV Gene Transfectants and T4 Endonuclease V-Liposome Recipients", *Photochemistry and Photobiology*, vol. 54, pp. 753-760, 1991.
Kripke et al., "Pyrimidine dimers in DNA initiate systemic immunosuppression in UV-irradiated mice", *Proc. Natl. Acad. Sci. U.S.A.*, vol. 89, pp. 7516-7520, Aug. 1992.
Yarosh et al., "Enhancement of DNA Repair of UV Damage in Mouse and Human Skin by Liposomes Containing a DNA Repair Enzyme", *J. Soc. Cosmet. Chem.*, vol. 41, pp. 85-92, Jan./Feb. 1990.
Yarosh et al., "Pyrimidine Dimer Removal Enhanced by DNA Repair Liposomes Reduces the Incidence of UV Skin Cancer in Mice", *Cancer Research*, vol. 52, pp. 4227-4231, 1992.
Yarosh et al., "Effect of T4N5 Liposome-Enhanced DNA Repair on UV-Induced Transcription from the HIV Promoter", Abstract of the Proceedings of the 20th Annual Meeting of the American Society for Photobiology, Marco Island, Fla., Jun. 20-24, 1992, p. 80S.

*Primary Examiner*—G. S. Kishore
*Attorney, Agent, or Firm*—Maurice M. Klee

[57] ABSTRACT

A method for tanning skin is provided in which liposomes containing a DNA repair enzyme are administered to skin in combination with exposure of the skin to UV radiation. The result is an enhanced level of melanin production, i.e., more tanning than achieved by UV radiation alone. The administration of the DNA repair enzymes in liposomes also reduces the level of DNA damage caused by the UV exposure. Accordingly, both the tanning response is increased and the deleterious effect of UV exposure is decreased. The method can be used by the general population as well as by individuals whose skin is susceptible to UV-induced damage.

23 Claims, 5 Drawing Sheets

TANNING METHOD USING DNA REPAIR LIPOSOMES

BACKGROUND OF THE INVENTION

1. Field of the Invention

This invention relates to a method for enhancing UV tanning of skin using liposomes and, in particular, liposomes containing one or more DNA repair enzymes (hereinafter referred to as "DNA repair liposomes").

2. Description of the Prior Art

Tanning is the natural response of human and animal skin to exposure to UV radiation and involves enhanced production and distribution by melanocytes of the protein melanin in the skin. Biochemically, melanin is produced by polymerization of oxidation products of tyrosine and dihydroxyphenyl compounds, e.g., dopa.

Tanning has both a cosmetic and clinical value. Cosmetically, tanned skinned is considered desirable by many people as evidenced by the widespread use of tanning lotions, tanning parlors, and the popularity of recreational sunbathing. Clinically, tanned skin is more resistant to the deleterious effects of sunlight than untanned skin. For example, people with more pigmented skin tend to suffer a lower incidence of skin cancer.

In view of these facts, there have been continuing efforts to develop methods and materials which will enhance tanning. The ideal tanning system would be one which both increases the tanning response and decreases the deleterious effects of sun exposure. The present invention is directed to providing such a system.

SUMMARY OF THE INVENTION

In view of the foregoing, it is an object of the invention to provide methods and materials for enhancing the tanning of skin. It is a further object of the invention to provide such methods and materials which have the capability of also repairing damage to the skin caused by sun exposure.

To achieve the foregoing and other objects, the invention in accordance with certain of its aspects provides a method for enhancing tanning of skin comprising the steps of:

(a) exposing the skin to UV radiation; and (b) applying liposomes containing at least one DNA repair enzyme to the skin, said liposomes being applied to the skin before and/or during and/or after the exposure to UV radiation in an amount effective to cause enhanced tanning of the skin in comparison to the level of tanning of the skin upon exposure to the same dose of UV radiation in the absence of said liposomes.

In certain preferred embodiments of the invention, the skin to be tanned is exposed to repeated doses of UV radiation. In other preferred embodiments, the DNA repair enzyme comprises T4 endonuclease V, a photolyase, or mixtures thereof.

As discussed in detail below, the mechanism of this enhanced tanning is through the enhanced production of melanin by melanocytes after the combination of UV exposure and the administration of DNA repair liposomes. This enhanced production of melanin by melanocytes is itself one of the aspects of the invention.

In addition to their use with the general population, DNA repair liposomes can in particular be used to protect the skin of individuals susceptible to UV-induced damage by promoting tanning of such skin upon UV exposure while reducing damage to the skin caused by such exposure.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

DESCRIPTION OF THE PREFERRED EMBODIMENTS

Figure 1:
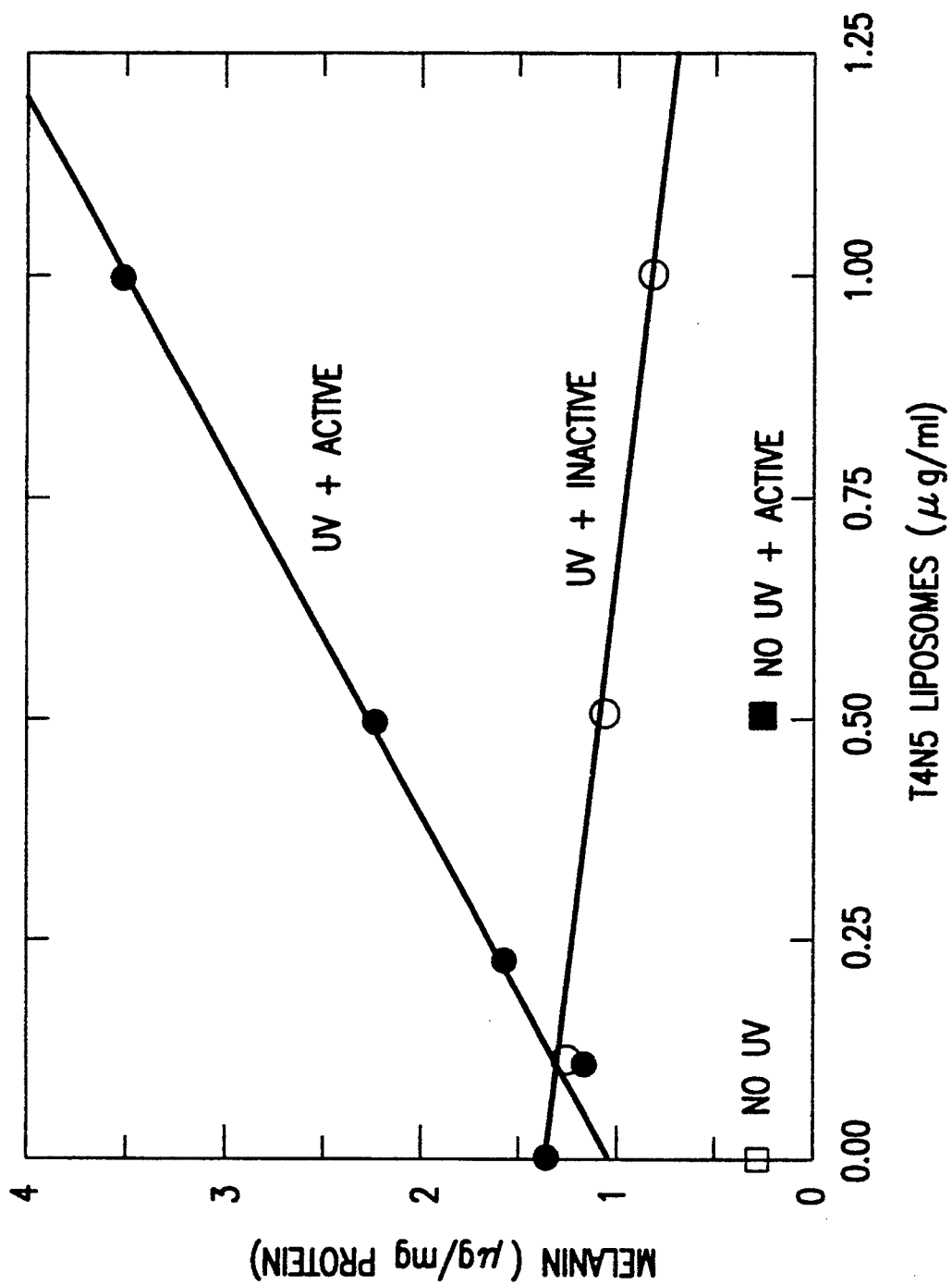
FIG. 1 is a dose response curve showing increased melanin production with increasing concentration of DNA repair liposomes.

As discussed above, the present invention relates to the combined steps of exposing skin to UV radiation and applying liposomes containing one or more DNA repair enzymes to the skin.

The UV exposure can be either from natural sunlight or artificial sources or a combination thereof. Natural sunlight contains UV-A and UV-B, where UV-A has a wavelength of approximately 320 nanometers to, approximately 380 nanometers and UV-B has a wavelength of approximately 280 nanometers to approximately 320 nanometers. The light coming from the sun also includes UV-C which is normally absorbed by the earth's ozone layer.

UV-B is more effective than UV-A in inducing tanning. Accordingly, if an artificial source is used to provide the UV exposure, to be most effective, the source should be designed to produce IIV-B. However, due to health concerns regarding I/V-B, artificial sources which are skewed toward the UV-A spectrum are, in general, preferred for human applications of the invention.

In terms of inducing melanocytes to produce melanin in vitro, I/V-B will normally be employed. Melanin production by melanocytes in situ follows the same guidelines as for tanning, i.e., the production can be induced either with natural sunlight, an artificial source of the type described above, or a combination thereof.

The DNA repair liposomes are preferably prepared following the procedures of Yarosh, U.S. Pat. No. 5,077,211 and PCT patent publication No. WO 90/00598, the relevant portions of which are incorporated herein by reference. In particular, pH sensitive liposomes composed of phosphatidyl choline, phosphatidyl ethanolamine, oleic acid, and cholesteryl hemisuccinate in a 2:2:1:5 molar ratio are preferred for the practice of the present invention.

The DNA repair enzymes are encapsulated in the liposomes using, for example, the procedures of the above referenced Yarosh patent and patent publication. Either a single DNA repair enzyme or a mixture enzymes can be used in the practice of the invention.

When a mixture is used, it can be formed by separately encapsulating individual enzymes in liposomes or by mixing the set of enzymes prior to encapsulation.

Purified DNA repair enzymes are preferably used in the practice of the invention, although cell extracts containing DNA repair enzymes can be used if desired. Purification can be accomplished using the techniques of the above identified Yarosh patent and patient publication or other techniques as desired. The purification and encapsulation techniques used must maintain at least some of the biological activity of the DNA repair enzyme and preferably most of that activity.

The DNA repair enzyme or enzymes will normally be of the type which can repair UV-damaged DNA. Examples of such enzymes include the photolyases, the UV-DNA endonucleases, UV-DNA helicases, the UV-DNA base excision repair glycosylases, apurinic/apyrimidinic endonucleases, and similar enzymes now known or subsequently identified. Preferred DNA repair enzymes are T4 endonuclease V which is produced by phage T4 and has UV-DNA base excision repair glycosylase activity and the photolyases. These enzymes are preferably used alone, although if desired can be used in combination with each other or with other DNA repair enzymes. In the case of the photolyases, after application, the enzyme needs to be exposed to visible light for activation.

For topical applications, the DNA repair liposomes are incorporated in a suitable vehicle. Since the liposomes are composed of lipids, the vehicle should be of the type in which lipids are not substantially soluble to avoid dissolving the liposome membranes. e.g., the vehicle should be water based and should not include detergents. In the case of pH sensitive liposomes, the vehicle should be buffered to a pH above the pH at which the liposome membranes are destabilized. e.g., a pH of 7 or greater. Examples of suitable vehicles include the hydrogels HYPAN SS201 produced by Kingston Hydrogels, Dayton, New Jersey, and CARBOPOL-941 produced by B. F. Goodrich, Brecksville, Ohio. To form the vehicle, these hydrogels are neutralized with triethanolamine and hydrated with phosphate buffered saline to a final concentration of 1.5% w/v.

Typical concentrations of enzyme and lipid in the solution used to prepare the liposomes are from about 0.1 to about 10.0 mg/ml for the enzyme and approximately 10 millimolar for the lipids. The concentration of enzyme in the finished composition is typically in the range from about 0.1 to about 10.0 $\mu g/ml$. A typical dosage of the final composition for application to the skin is in the range from about 20 to about 100 $\mu l/cm^2$. Other concentrations and dosages can be used in the practice of the invention if desired.

As discussed above, one of the aspects of the invention involves inducing melanocytes to produce melanin. This can be done for melanocytes in living skin in which case the above enzyme, liposome, and vehicle concentrations can be used. Alternatively, the induction can be performed on a cell culture of melanocytes or their derivatives, such as, melanoma cells, in which cased the DNA repair liposomes are administered to the target cells in a suitable cell culture medium such as RPMI-1640. As discussed below in Example 4, it has been found that melanin production is inhibited by the presence of tyrosine in the cell culture medium. Accordingly, the medium for the DNA repair liposomes should not contain substantial amounts of this amino acid. Similarly, the vehicle used for application of the DNA repair liposomes to living skin should have a low concentration of tyrosine.

As discussed above, the present invention is based on a combination of UV exposure and administration of DNA repair liposomes to living skin cells. As demonstrated by the examples presented below, it has been surprisingly found that DNA repair liposomes increase the amount of melanin produced by melanocytes upon exposure of the skin and/or melanocytes to radiation. That is, melanocytes when exposed to UV in the absence of DNA repair liposomes produce melanin at a first level and when exposed to the same dose of UV radiation in the presence of DNA repair liposomes produce melanin at a second level greater than the first level. Moreover, it has been found that the second level of melanogenesis varies with the concentration of DNA repair liposomes in a dose dependent manner. In particular, for a constant UV exposure, the level of melanogenesis has been found to increase substantially linearly with the concentration of DNA repair liposomes.

It should be noted that DNA repair liposomes themselves, i.e., without UV exposure, do not result in the production of melanin, although repair of endogenous DNA damage may occur. Thus, the present invention is dependent on the combination of the acts of UV exposure and administration of DNA repair liposomes. When these two acts are both performed, the result is enhanced melanin production and enhanced DNA repair; when only UV exposure is performed, only the first level of melanin production is achieved and there is no increase in DNA repair; when only administration of DNA repair liposomes is performed, essentially no melanin is induced, although repair of endogenous DNA damage may occur.

In terms of tanning, these results mean that for the same amount of UV exposure, an individual can achieve a darker tan by using DNA repair liposomes than he or she would have achieved without such liposomes, and such darker tan is achieved with less DNA damage. Alternatively, an individual can achieve the same level of tanning with less UV exposure and less DNA damage. Thus, the two benefits of an ideal tanning system are achieved by means of the invention—an increase in tanning response and a decrease in the deleterious effects of sun exposure.

Similar benefits are achieved in the clinical applications of the invention. In this case, the invention is used with individuals whose skin is susceptible to UV-induced damage. Examples of such individuals are people with Fitzpatrick Type I skin which upon UV exposure usually burns and rarely tans and those with Type II skin which tans only moderately. Since sun exposure is unavoidable, these people benefit from the invention because with the invention they achieve tanned skin and thus the natural benefits of skin pigmentation under conditions where their skin would not have tanned equally without the invention. Also, these individuals achieve the tanned condition with less DNA damage than would have occurred if their skin had been exposed to the same level of UV radiation without the application of DNA repair liposomes.

The two components of the invention can occur in a variety of temporal sequences. For example, the UV exposure can occur before, during, and/or after the application of the DNA repair liposomes. Thus, in the case of tanning, the user can apply the composition of the invention to his or her skin before or during sunbathing or in the evening after a typical day of sunbathing. When applying the DNA repair liposomes prior to UV exposure, it is desirable to make the application shortly before exposure in view of the half-life of DNA repair enzymes in skin.

To maximize the tanning response while minimizing the deleterious effects of UV exposure, it is desirable to practice the invention by using a number of lower doses of UV radiation applied repetitively, rather than one large dose, with each of the smaller doses being followed or preceded by the administration of DNA repair liposomes. In general, the overall melanin response will be a function of the total UV exposure with greater exposure resulting in more melanin. Thus, as is commonly observed, more tanning is achieved by more sun exposure.

Without intending to limit it in any manner, the present invention will be more fully described by the following examples. The materials and methods which are common to the examples are as follows.

DNA REPAIR LIPOSOMES

T4N5 liposomes were prepared using the procedures described above. The liposomes contained approximately 0.2 mg/ml of T4 endonuclease V encapsulated in a membrane composed of phosphatidyl choline, phosphatidyl ethanolamine, oleic acid, and cholesteryl hemisuccinate in a 2:2:1:5 molar ratio.

PHOTOSOMES were similarly prepared and contained approximately 10 mg/ml of a cell extract which included the photolyase from *Anacystis nidulans*. The same lipids in the same molar ratios were used to prepare the PHOTOSOMES as were used to prepare the T4N5 liposomes.

The liposomes were suspended in phosphate buffered saline at a concentration of approximately 2 $\mu$g of encapsulated enzyme per milliliter of solution ($\mu$g/ml) for the T4N5 liposomes and approximately 1 mg/ml for the PHOTOSOMES.

CELL CULTURE

S91 Cloudman mouse melanoma cells were used to perform the experiments. They were grown in a humidified, 5% $CO_2$ atmosphere at 37° C. to subconfluence. The culture medium was either Dulbecco's modified Eagle's medium containing 10% newborn calf serum or RPMI-1640 medium with 15% fetal calf serum.

UV IRRADIATION

The UV-B source was an unfiltered FS-20 or FS-40 sunlamp at a fluence rate of 2 $J/m^2$/sec. For irradiation of the cells, the media was removed just prior to exposure and replaced directly thereafter.

MELANIN MEASUREMENT

Melanin levels in the S91 cells were determined by collecting the cells, washing them with phosphate buffered saline, and resuspending them 1N NaOH, with shaking for 1 hour. The resulting mixture was transferred to a cuvette and the optical density at either 475 or 492 nanometers was measured. A standard curve was prepared using commercially available melanin. To report levels of melanin per cell, a cell count was performed prior to the NaOH treatment. To report levels of melanin per milligram protein, the protein concentration in the extract after NaOH treatment was determined using the Bradford reaction.

EXAMPLE 1

Melanin Production versus UV Exposure

The effect of increased UV exposure was determined by irradiating S91 melanoma cells with varying amounts of UV-B. Six sets of plated cells were irradiated once each day for three consecutive days and analyzed for melanin production on the fourth day. The daily UV dose for the six sets were as follows: set 1–0 $J/m^2$; set 2–25 $J/m^2$; set 3–50 $J/m^2$; set 4–75 $J/m^2$; set 5–100 $J/m^2$; set 6–200 $J/m^2$.

The number of cells surviving treatment decreased to 2.3% for the highest dose, but the melanin content per surviving cell increased from 9.6 pg/cell in the unirradiated cells to 631 pg/cell for the cells of set 6. The increase in melanin content per surviving cell was found to be a substantially monotonic function of the UV dose.

EXAMPLE 2

Enhancement of Melanin Production by T4N5 Liposomes

The enhancement of melanin production by T4N5 liposomes was demonstrated by irradiating S91 cells with either 75 or 100 $J/m^2$ of UV-B and adding T4N5 liposomes to the irradiated cells at a concentration of 0.1 $\mu$g/ml. The Dulbecco's medium was used in these experiments. Plated cells were irradiated and treated with the DNA repair liposomes each day for four consecutive days and analyzed for melanin content on the fifth day.

The melanin content per cell increased from 0.3 pg/cell to 0.8 and 1.5 pg/cell upon irradiation of the cells with 75 and 100 $J/m^2$, respectively (no liposome treatment). With liposome treatment, the melanin content increased further to 1.2 and 5.5 pg/cell for the two UV doses.

This experiment shows that: 1) melanin production increases with T4N5 liposome treatment, i.e., from 0.8 to 1.2 pg/cell for a UV dose of 75 $J/m^2$ and from 1.5 to 5.5 pg/cell for a UV dose of 100 $J/m^2$; and 2) for constant liposome concentration, melanin production increases with UV dose, i.e., from 1.2 to 5.5 pg/cell.

EXAMPLE 3

Melanin Production versus DNA Repair Liposome Concentration

The effect of increased DNA repair liposome concentration was determined by irradiating S91 cells with 100 $J/m^2$ of UV-B and adding T4N5 liposomes to the irradiated cells at concentrations of 0.2 and 1.0 $\mu$g/ml. The RPMI-1640 medium was used in these experiments. Thee cells were irradiated and treated with liposomes each day for three consecutive days and analyzed for melanin content on the fourth day.

The melanin content per cell increased from 4.8 to 6.4 pg/cell upon irradiation of the cells with 100 $J/m^2$ (no liposome treatment). With liposome treatment, the melanin content increased further to 7.8 and 48.2 pg/cell for the two liposome concentrations.

This experiment shows that melanin production increases with increasing amounts of DNA repair liposomes.

EXAMPLE 4

Effect of Tyrosine on Melanin Production

A comparison of Examples 2 and 3 shows that the baseline and induced levels of melanin production were higher when RPMI-1640 medium was used than when Dulbecco's medium was used. Also, significant variability in the data was observed with the Dulbecco's medium and the data of Example 2 represents the positive results achieved.

Experiments using isobutylmethylxanthine to induce melanin production were performed to determine the effect of the medium on melanin production. The results confirmed that the RPMI-1640 medium is better than the Dulbecco's medium.

The most significant difference between the two media is that the Dulbecco's medium contains 103.8 mg/L of L-tyrosine.2Na.2H$_2$O, while the RPMI-1640 medium has only 28.8 mg/L of this amino acid. Based on these experiments, the DNA repair liposomes of the invention are preferably administered in a medium or vehicle having a low concentration of L-tyrosine.

EXAMPLE 5

Dose Response Curve

A dose response curve was prepared by irradiating S91 cells with 100 J/m$^2$ of UV-B and adding T4N5 liposomes to the irradiated cells at concentrations of 0.0, 0.1, 0.2, 0.5 and 1.0 µg/ml. As a control, liposomes were prepared which encapsulated heat-inactivated T4 endonuclease V (hereinafter "inactive liposomes") at concentrations of 0.1, 0.5, and 1.0 µg/ml. The RPMI-1640 medium was used in these experiments. The cells were irradiated and treated with the active and inactive liposomes each day for three consecutive days and analyzed for melanin content on the fourth day.

The results are shown in FIG. 1. As shown therein, in the absence of liposomes, UV irradiation caused an increase in melanin production from 0.3 µg of melanin per mg of cell extract protein (µg/mg) to 1.35 µg/mg. In the absence of irradiation, addition of 0.5 µg/ml of active T4N5 liposomes produced essentially no change in melanin production. Similarly, the additional of inactive liposomes at concentrations of 0.1, 0.5, and 1.0 µg/ml to UV-irradiated cells had no substantial, effect.

The combination of UV radiation and active DNA repair liposomes, however, had a dramatic effect. As shown in FIG. 1, the melanin production increased substantially linearly with liposome concentration reaching a level three times greater at a liposome concentration of 1.0 µg/ml than that achieved in the absence of active liposomes.

Figure 2:
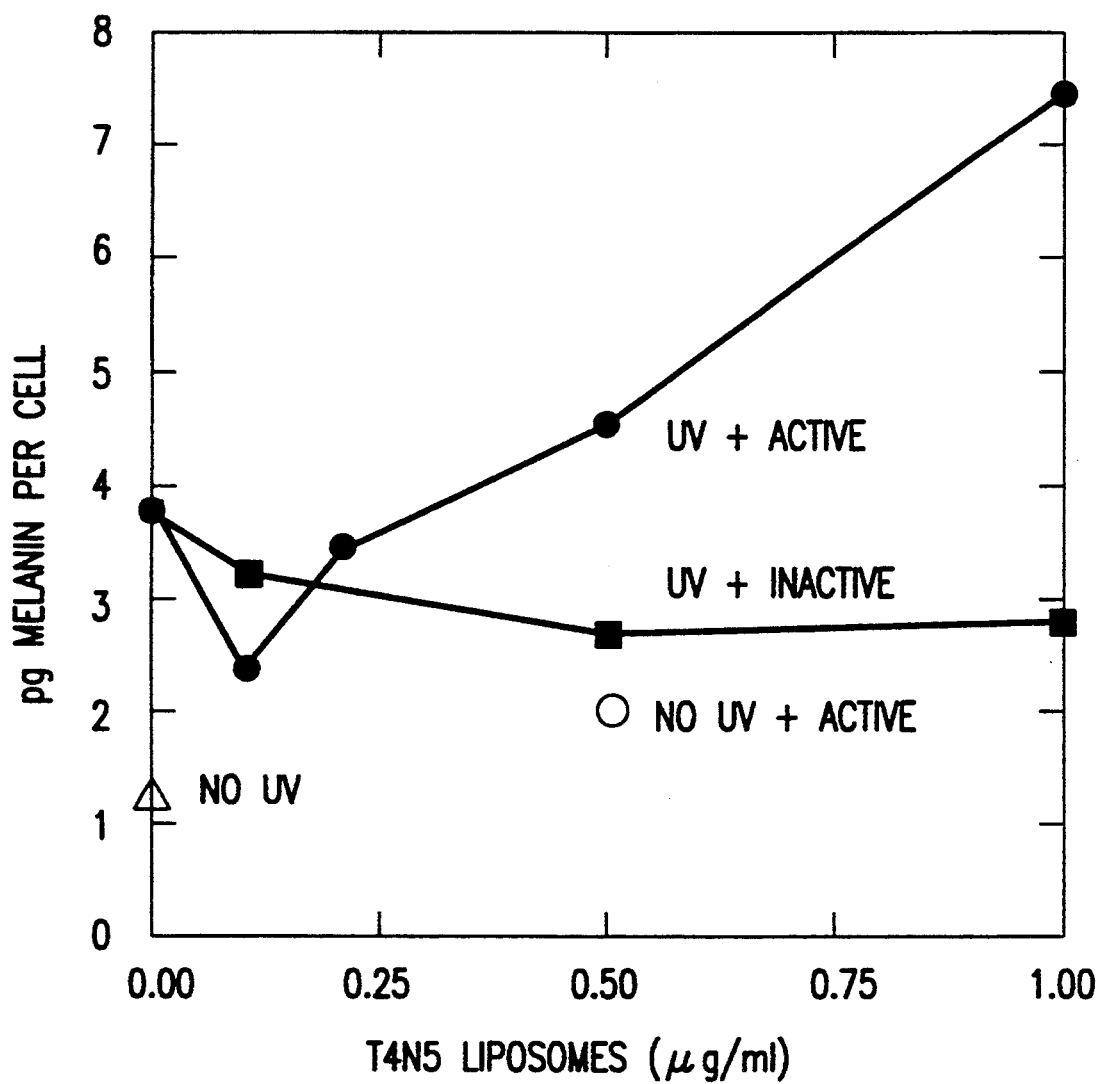
FIG. 2 shows the same data as FIG. 2 but in terms of pg melanin per cell rather than µg melanin per mg protein.

For the purpose of comparison with prior examples, the data of FIG. 1 has been replotted in FIG. 2 on a pg melanin per cell basis rather than µg/mg cell protein as in FIG. 1. The dramatic effect of the active DNA repair liposomes is again clear from this figure.

EXAMPLE 6

Cytokine Investigations

Experiments were performed to determine if cytokines are involved in the induction of melanin production by the combination of UV radiation exposure and DNA repair liposome application. In particular, studies were performed using the cytokines TNF-α, gamma-interferon, IL-1β, and IL-10. The cytokines were added to the S91 cultures at various concentrations and melanin production was measured. The cultures were not exposed to UV.

Some effect, i.e., some increase in melanin production, was observed for TNF-α at a concentration of about 500 units/ml. However, at 1000 units/ml and for concentrations less than 400 units/ml no effect was seen. A similar pattern was seen for IL-1β around a concentration of 25 units/ml and for IL-10 around 20 nanograms/ml. No effect was seen for gamma-interferon.

In order to investigate further soluble mediators which may increase melanin production, Pam-212 mouse keratinocytes were irradiated with UV-B doses of 50, 100, or 200 J/m$^2$ and then co-cultivated with unirradiated mouse S91 melanoma cells in the same cell culture dish. A detectable increase in melanin production by the melanoma cells was observed with increasing UV dose to the keratinocytes, but the total increase was less than a doubling of melanin levels, i.e., an increase from 1.5 pg/cell to 2.4 pg/cell.

As a further test of this effect, S91 cells were grown in wells of plastic dishes and Pam-212 cells were grown on membranes with pores of 0.2 µ, which allow the passage of molecules such as mediators but not whole cells. The Pam-212 cells on the membranes were UV-B irradiated with 100 J/m$^2$ UV-B and then the membranes were inserted into the wells containing the S91 cells. This allowed soluble mediators produced by the Pam-212 cells to pass to the S91 cells, without cell passage or physical contact of the two cell types. A less than doubling in melanin levels was found in those wells which contained irradiated Pam-212 cells compared to unirradiated cells, increasing from 1.0 pg/cell to 1.8 pg/cell.

EXAMPLE 7

Enhancement of DNA Repair by DNA Repair Liposome Lotions

The enhancement of DNA repair using a lotion containing T4N5 liposomes was demonstrated by irradiating SKH-1 albino hairless female mice with either 1200 or 400 J/m$^2$ of UV-B, three times a week for thirty weeks. Immediately after each UV exposure, T4N5 liposomes in a lotion consisting of either 5% dextran for the 1200 J/m$^2$ experiment or 1% HYPAN SS201 hydrogel for the 400 J/m$^2$ test were applied to the back of each mouse with a moist cotton swab. The use of albino mice allows for separation of the DNA repair effect of DNA repair liposomes from the protective effect of melanin production induced by those liposomes.

Each week the mice were examined and lesions greater than 1 millimeter in diameter were recorded. Invariably, lesions greater than 1 millimeter are squamous cell carcinomas in this system as determined by histopathology. The incidence of skin cancer was determined as the fraction of surviving mice with at least one tumor and the mean time to first tumor was calculated from the Weibull survival distribution.

Figure 3A:
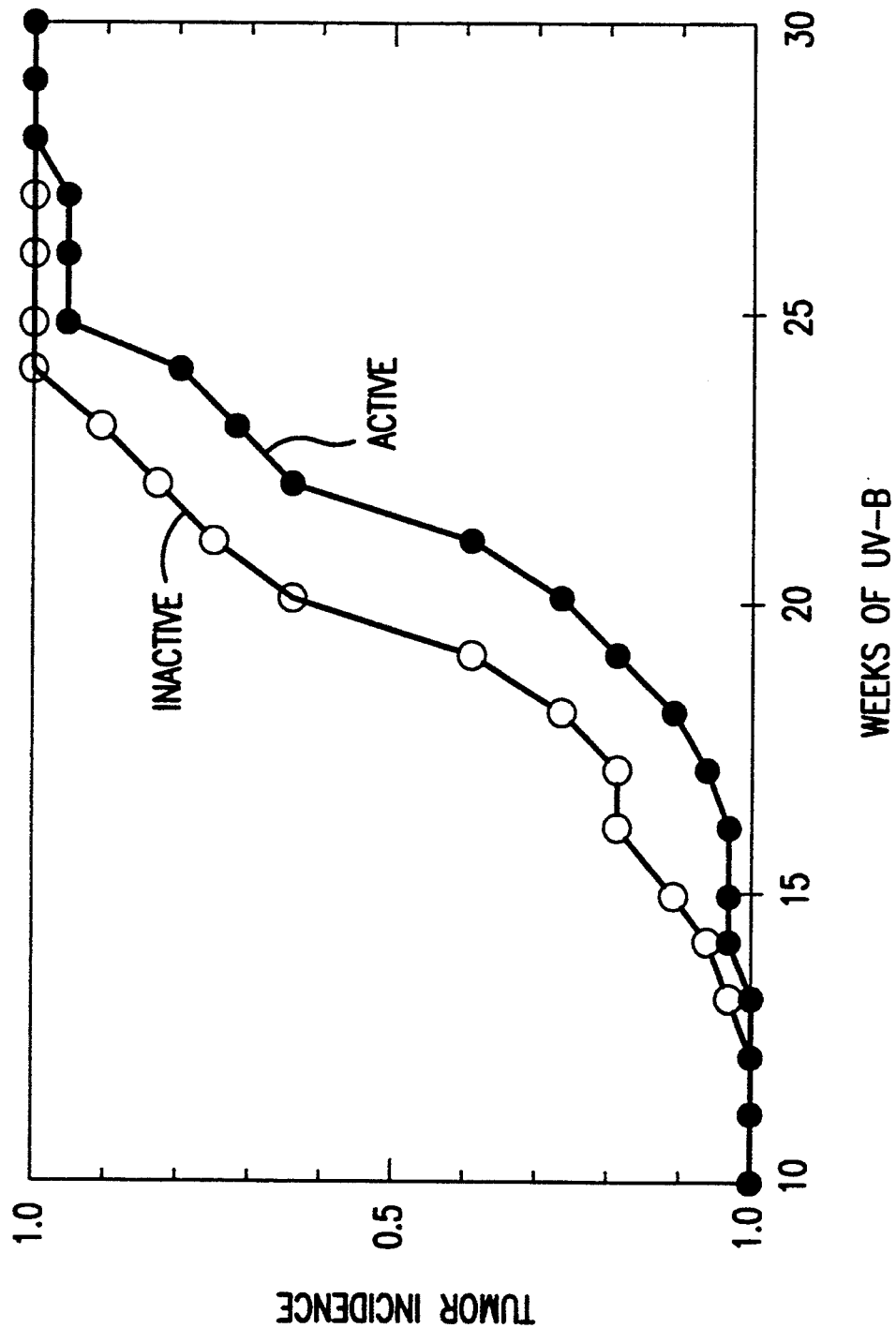
FIG. 3A—3C demonstrate the ability of DNA repair liposome lotions to protect mouse skin from UV damage.
Figure 3B:
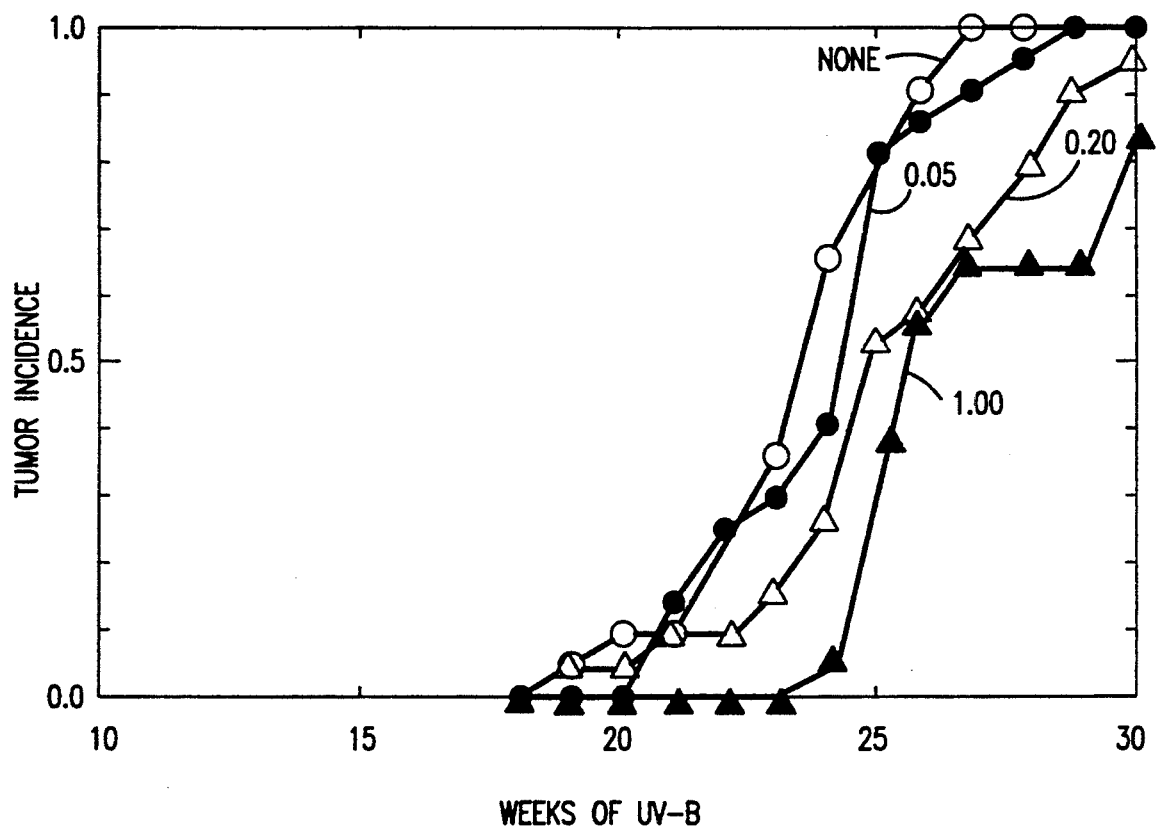
Figure 3C:
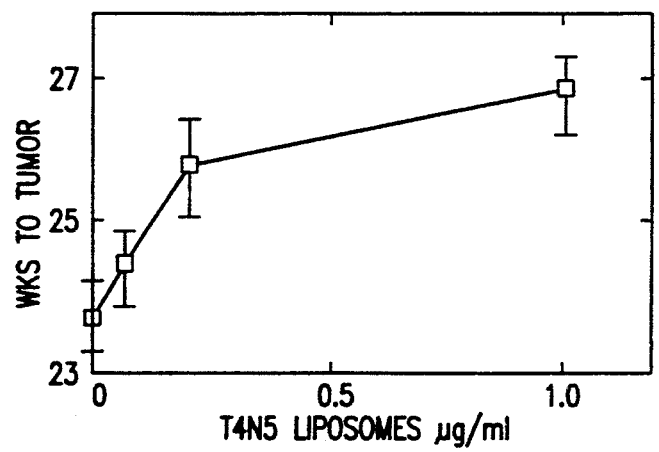

The results of these experiments are shown in FIG. 3 where tumor incidence is plotted against weeks of UV exposure. Panel A shows the results for the 1200 J/m$^2$ experiment, and panel B, those for the 400 J/m$^2$ exposure. As shown in Panel A, animals treated with active T4N5 liposome lotion had a lower tumor incidence and a longer mean time to first tumor (closed circle data points) than animals treated with inactive liposome lotion at the same concentration (open circle data points). Panel B shows that the tumor incidence decreases monotonically with increasing concentration of the active DNA repair liposomes in the lotion. The insert in this panel is a dose response curve calculated from the data of the 400 J/m$^2$ experiment and demonstrates that the mean time to first tumor increases with increasing liposome concentration.

Similar results have been obtained for human skin using a lotion containing PHOTOSOMES at a concentration of 10 µg/ml. In this case, the biological endpoint was the frequency of UV-induced cyclobutane pyrimidine dimers in DNA. The PHOTOSOMES were found to reduce the dimer frequency by 50% or greater.

EXAMPLE 8

Enhanced Tanning of Human Skin by DNA Repair Liposomes

A lotion containing DNA repair liposomes, specifically PHOTOSOMES at 10 µg/ml in a hydrogel base, was applied daily to one arm of normal human volunteers having outdoor occupations. As a control, a lotion containing inactive PHOTOSOMES was applied to the other arm.

After ten weeks, biopsies were taken from the control and test arms. The samples were fixed in 40% neutral buffered formaldehyde, embedded in paraffin and sectioned onto glass slides. The slides were dewaxed, stained for melanin by the Masson-Fontana technique, and examined by brightfield microscopy at 600 fold magnification.

The stained melanin appears as dark caps covering and surrounding the cells of the basal layer of the epidermis. In the section of the test biopsies, the melanin staining was consistently darker and more extensive than in the control portions.

Figure 4:
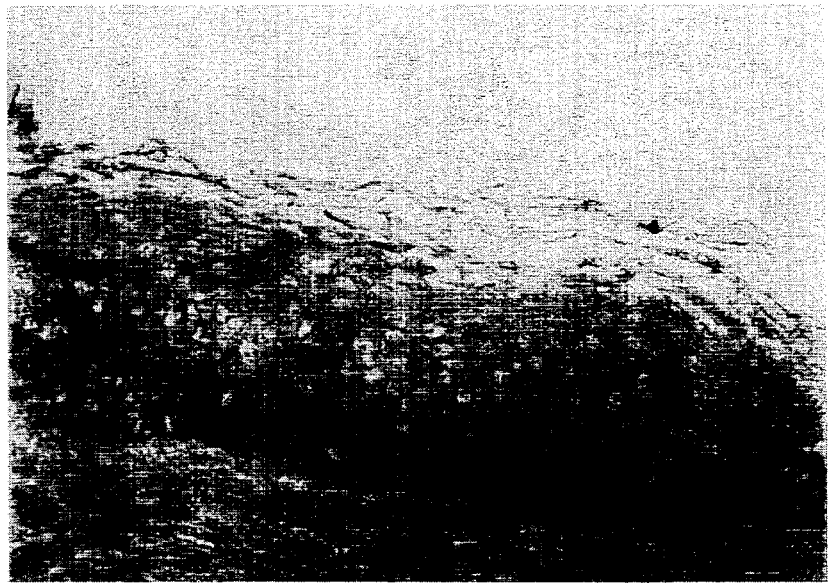
FIGS. 4 and 5 are photomicrographs showing enhanced tanning of human skin through the use of the present invention. The arrows next to these figures show the location of the melanin in the basal layer.

Examples of this consistent pattern are shown in FIG. 4. This figure is a photomicrograph of the sectioned biopsy from the PHOTOSOME-treated arm. At the top of the skin sample is the stratum corneum layer which appears as flaking shreds of keratin. The next layer is the upper epidermis, which appears as flattened, differentiated keratinocytes. At the bottom of the epidermis is the basal layer. In this photomicrograph the cells of the basal layer are surrounded and capped by darkly staining material, which is the melanin induced by PHOTOSOME treatment. Below this layer is the dermis.

Figure 5:
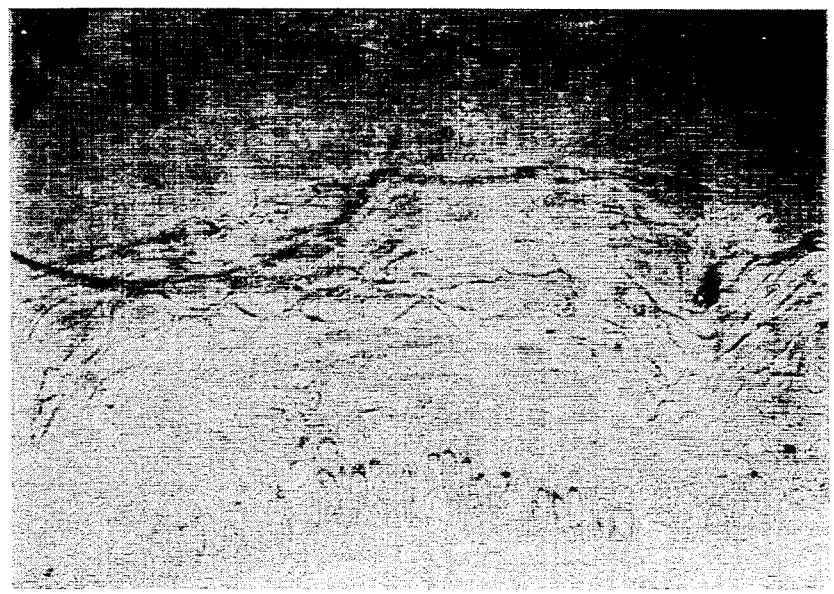

This photomicrograph showing the induced melanin in the basal layer is in contrast to the photomicrograph in FIG. 5 which shows the control sample taken from the opposing arm of the same subject. Much less melanin is visible in the basal layer of the epidermis. This pattern of enhanced melanin production in PHOTOSOME-treated skin demonstrates that combining UV-irradiation of human skin with administration of DNA repair liposomes increased tanning through the increased production of melanin.

Although preferred and other embodiments of the invention have been described herein, other embodiments may be perceived by those skilled in the art without departing from the scope of the invention as defined by the following claims.

What is claimed is:

1. A method for tanning skin comprising applying liposomes containing at least one DNA repair enzyme to skin in an amount effective to produce tanning or melanin production and exposing the skin to UV radiation, said applying of the liposomes occurring before and/or during and/or after the exposure to said UV radiation.

2. The method of claim 1 wherein the liposomes are applied to the skin before exposure to UV radiation.

3. The method of claim 1 wherein the liposomes are applied to the skin during exposure to UV radiation.

4. The method of claim 1 wherein the liposomes are applied to the skin after exposure to UV radiation.

5. The method of claim 1 wherein the skin is repetitively exposed to UV radiation.

6. The method of claim 1 wherein the liposomes are suspended in a hydrogel.

7. The method of claim 1 wherein the at least one DNA repair enzyme comprises T4 endonuclease V.

8. The method of claim 1 wherein the at least one DNA repair enzyme comprises a photolyase.

9. A method for inducing melanin production by melanocytes comprising administering liposomes containing at least one DNA repair enzyme in an amount effective to induce melanogenesis to melanocytes and exposing the melanocytes to UV radiation, said administering of the liposomes occurring before and/or during and/or after the exposure to said UV radiation.

10. The method of claim 9 wherein the liposomes are to the melanocytes before exposure to UV radiation.

11. The method of claim 9 wherein the liposomes are administered to the melanocytes during exposure to UV radiation.

12. The method of claim 9 wherein the liposomes are administered to the melanocytes after exposure to UV radiation.

13. The method of claim 9 wherein the melanocytes are repetitively exposed to UV radiation.

14. The method of claim 9 wherein the at least one DNA repair enzyme comprises T4 endonuclease V.

15. The method of claim 9 wherein the at least one DNA repair enzyme comprises a photolyase.

16. A method for protecting the skin of an individual susceptible to UV-induced damage comprising applying liposomes containing at least one DNA repair enzyme to the individual's skin in an amount effective to produce tanning or melanin production and exposing the individual's skin to UV radiation whereby the individual's skin becomes tanned, said applying of the liposomes occurring before and/or during and/or after the exposure to said UV radiation.

17. The method of claim 16 wherein the liposomes are applied to the skin before exposure to UV radiation.

18. The method of claim 16 wherein the liposomes are applied to the skin during exposure to UV radiation.

19. The method of claim 16 wherein the liposomes are applied to the skin after exposure to UV radiation.

20. The method of claim 16 wherein the skin is repetitively exposed to UV radiation.

21. The method of claim 16 wherein the liposomes are suspended in a hydrogel.

22. The method of claim 16 wherein the at least one DNA repair enzyme comprises T4 endonuclease V.

23. The method of claim 16 wherein the at least one DNA repair enzyme comprises a photolyase.

* * * * *